US012788689B2

(12) United States Patent
Angermann et al.

(10) Patent No.: US 12,788,689 B2
(45) Date of Patent: *Nov. 10, 2026

(54) DENTAL MATERIALS FOR THE PRODUCTION OF TEMPORARY CROWNS AND BRIDGES

(71) Applicant: Ivoclar Vivadent AG, Schaan (LI)

(72) Inventors: Jörg Angermann, Sargans (CH); Thomas Köhler, St. Margrethen (CH); Johannes Schädlich, Reichenau (DE)

(73) Assignee: Ivoclar Vivadent AG, Schaan (LI)

( * ) Notice: Subject to any disclaimer, the term of this patent is extended or adjusted under 35 U.S.C. 154(b) by 743 days.

This patent is subject to a terminal disclaimer.

(21) Appl. No.: 17/573,985

(22) Filed: Jan. 12, 2022

(65) Prior Publication Data

US 2022/0226200 A1 Jul. 21, 2022

(30) Foreign Application Priority Data

Jan. 21, 2021 (EP) .................................... 21152826

(51) Int. Cl.

| | |
|---|---|
| ***A61K 6/887*** | (2020.01) |
| ***A61C 5/70*** | (2017.01) |
| ***A61C 13/00*** | (2006.01) |
| ***A61K 6/30*** | (2020.01) |
| ***A61K 6/61*** | (2020.01) |

(52) U.S. Cl.

CPC ................ *A61K 6/887* (2020.01); *A61C 5/70* (2017.02); *A61C 13/0003* (2013.01); *A61K 6/30* (2020.01); *A61K 6/61* (2020.01)

(58) Field of Classification Search

CPC . A61K 6/887; A61K 6/30; A61K 6/61; A61C 5/70; A61C 13/0003

See application file for complete search history.

(56) References Cited

U.S. PATENT DOCUMENTS

| | | | | |
|---|---|---|---|---|
| 3,991,008 | A | 11/1976 | Temin et al. | |
| 6,815,470 | B2 | 11/2004 | Ibaragi et al. | |
| 7,275,932 | B2 | 10/2007 | Jin et al. | |
| 7,498,367 | B2 | 3/2009 | Qian | |
| 8,247,470 | B2 | 8/2012 | Yarimizu et al. | |
| 9,889,070 | B2 * | 2/2018 | Kashiki | C08F 22/38 |
| 11,141,354 | B2 | 10/2021 | Moszner et al. | |
| 11,141,356 | B2 | 10/2021 | Moszner et al. | |
| 2007/0040151 | A1 | 2/2007 | Utterodt et al. | |
| 2007/0100019 | A1 | 5/2007 | Sun | |
| 2010/0311864 | A1 | 12/2010 | Arita et al. | |
| 2017/0128328 | A1 * | 5/2017 | Moszner | A61K 6/61 |
| 2020/0253837 | A1 | 8/2020 | Moszner et al. | |

* cited by examiner

*Primary Examiner* — Alma Pipic

(74) *Attorney, Agent, or Firm* — Ann M. Knab; Thad McMurray

(57) ABSTRACT

Radically polymerizable dental material, which includes a combination of at least three thiourea derivatives, a hydroperoxide and preferably a transition metal compound as initiator system for the radical polymerization.

14 Claims, 2 Drawing Sheets

DENTAL MATERIALS FOR THE PRODUCTION OF TEMPORARY CROWNS AND BRIDGES

CROSS-REFERENCE TO RELATED APPLICATIONS

This application claims priority to European Patent Application No. 21152826.0 filed on Jan. 21, 2021, the disclosure of which is incorporated herein by reference in its entirety.

TECHNICAL FIELD

The present invention relates to radically polymerizable compositions with improved setting behaviour which are particularly suitable as dental materials, in particular as prosthesis materials for the production of temporary crowns and bridges. The compositions contain a redox system as initiator for the radical polymerization, which comprises a hydroperoxide and at least two different thiourea derivatives.

BACKGROUND

For the production of dental restorations and in particular for the production of temporary restorations, such as e.g. temporary crowns and bridges, polymerizable compositions based on radically polymerizable monomers are normally used. Mixtures of mono- and multifunctional (meth)acrylates are usually used as monomers. Dimethacrylates often used are 2,2-bis[4-(2-hydroxy-3-methacryloyloxypropyl) phenyl]propane (bis-GMA) and 1,6-bis-[2-methacryloyloxyethoxycarbonylamino]-2,2,4-trimethylhexane (UDMA), which have a high viscosity and result in polymerizates with very good mechanical properties. These are diluted with low-viscosity monomers such as triethylene glycol dimethacrylate (TEGDMA), 1,10-decanediol dimethacrylate (D3MA) and bis(3-methacryloyloxymethyl)tricyclo-[5.2.1.02.6]decane (DCP). For the hardening, suitable initiators are added, wherein photoinitiators, thermal initiators, redox initiator systems or combinations thereof are used depending on the field of use. Materials for the production of temporary crowns and bridges usually contain redox systems.

In order to guarantee a sufficient storage stability of the materials, materials based on redox initiators are usually used as so-called two-component systems (2C systems), wherein the oxidant (peroxide or hydroperoxide) and the reducing agent (amines, sulfinic acids, barbiturates, thiourea etc.) are each incorporated into separate components. These components are mixed with each other shortly before use. The components must be matched such that they can be easily mixed with each other homogeneously and are easy to handle. Moreover, there must be a processing time sufficient for dental purposes. By the processing time is meant the period of time between the blending of the components and the start of hardening of the mixed material.

For the production of temporary crowns or bridges, an impression of the tooth or teeth to be treated is made. Then the tooth or teeth are ground, the impression is then filled with a self-curing restoration material and pressed onto the prepared teeth. After the hardening, the material is removed from the impression and reworked by trimming with a scalpel or scissors or by milling. This is best achieved when the material is still elastic. If the hardening has progressed too far, the material is hard and brittle, which makes the post-processing difficult and can result in the cracking of the temporary prosthesis and in sharp edges. Materials for the production of temporary restorations are therefore to have an elastic phase that is as long as possible during the hardening.

Self-curing restoration materials often contain redox initiator systems which are based on a mixture of dibenzoyl peroxide (DBPO) with tertiary aromatic amines, such as e.g. N,N-diethanol-p-toluidine (DEPT), N,N-dimethyl-sym.-xylidine (DMSX) or N,N-diethyl-3,5-di-tert.-butylaniline (DABA). With such redox initiator systems the processing and curing time can be set relatively well in combination with phenolic inhibitors. A disadvantage of DBPO/amine systems is the discolorations which are caused by a slow oxidation of the amines.

Hydroperoxide redox initiator systems do not have this disadvantage because no amines are needed as reducing agent. Moreover, hydroperoxides are more thermally stable than peroxides. DE 26 35 595 C2 and corresponding U.S. Pat. No. 3,991,008, which US patent is incorporated by reference in its entirety, disclose polymerizable dental filling compounds which contain a substituted thiourea reducing agent in combination with a hydroperoxide as oxidant as initiator system. The materials are said to have an improved colour stability, an excellent cure rate and an improved storage stability.

EP 1 693 046 B1 and corresponding U.S. Pat. No. 7,498,367, which US patent is incorporated by reference in its entirety, disclose dental cements and core build-up materials which contain a (2-pyridyl)-2-thiourea derivative in combination with a hydroperoxide, in which the hydroperoxide group is bonded to a tertiary carbon atom.

WO 2007/016508 A1 and US 20070100019, which US published application is incorporated by reference in its entirety, disclose polymerizable dental compositions which contain a hydroperoxide in combination with a thiourea derivative and 2-mercapto-1-methylimidazole as initiator system. The materials are characterized by the fact that they do not contain acid group-containing components.

According to EP 1 754 465 B1 and US 20070040151 A1, which US published application is incorporated by reference in its entirety, the cumene hydroperoxide/acetyl thiourea system is said to have unusably slow curing kinetics. The addition of soluble copper compounds is proposed to overcome this problem.

U.S. Pat. No. 7,275,932 B2, which is incorporated by reference in its entirety, proposes the use of hydroperoxides and thiourea derivatives in combination with an acid compound as accelerator. Preferred acid compounds are acrylates and methacrylates with acid groups such as e.g. methacrylic acid.

EP 2 233 544 A1 and corresponding U.S. Pat. No. 8,247,470, and EP 2 258 336 A1 and corresponding US 20100311864, which US patent and published application are incorporated by reference in their entirety, disclose dental materials which contain a hydroperoxide and a thiourea derivative in combination with a vanadium compound as accelerator.

To avoid the disadvantages associated with organic peroxides and tertiary amines, U.S. Pat. No. 6,815,470 B2, which is incorporated by reference in its entirety, proposes the use of an aryl borate in combination with an acid compound and a peroxide as initiator system. By reaction with the acid compound, the aryl borate is said to form an aryl borane which releases polymerizable radicals when reacted with oxygen. Polymerizable monomers which have acid groups can be used as acid compound.

EP 3 692 975 A1 and U.S. Ser. No. 11/141,356, which US patent is incorporated by reference in its entirety, disclose radically polymerizable dental materials which contain a combination of a thiourea derivative, a hydroperoxide and a peroxide as initiator system for the radical polymerization. The reactivity of an initiator system based on a hydroperoxide and a thiourea derivative can be considerably accelerated by the addition of a small quantity of a peroxide.

EP 3 692 974 A1 and U.S. Ser. No. 11/141,354, which US patent is hereby incorporated by reference in its entirety, disclose radically polymerizable dental materials with an initiator system for the radical polymerization which additionally comprises at least one transition metal compound in addition to a thiourea derivative, a hydroperoxide and a peroxide. The mechanical properties of the materials after hardening can be substantially improved by the addition of the transition metal compound.

Low-odour hydroperoxides which are suitable in combination with a thiourea derivative as initiators for radically polymerizable dental materials are known from EP 3 692 976 A1 and US 20200253837, which US published application is hereby incorporated by reference in its entirety.

SUMMARY

The object of the invention is to provide dental materials which have a processing time suitable for dental purposes and a high storage stability, which pass through a long elastic phase during hardening and which have good mechanical properties after complete hardening. The materials are to be suitable in particular for the production of temporary dental restorations such as crowns and bridges.

According to the invention, this object is achieved by radically polymerizable dental materials which contain a hydroperoxide in combination with at least three different thiourea derivatives as initiator system.

BRIEF DESCRIPTION OF THE DRAWINGS

Exemplified embodiments of the invention are illustrated in the drawings and are described in more detail hereinunder. In the drawings.

DETAILED DESCRIPTION

Figure 1:
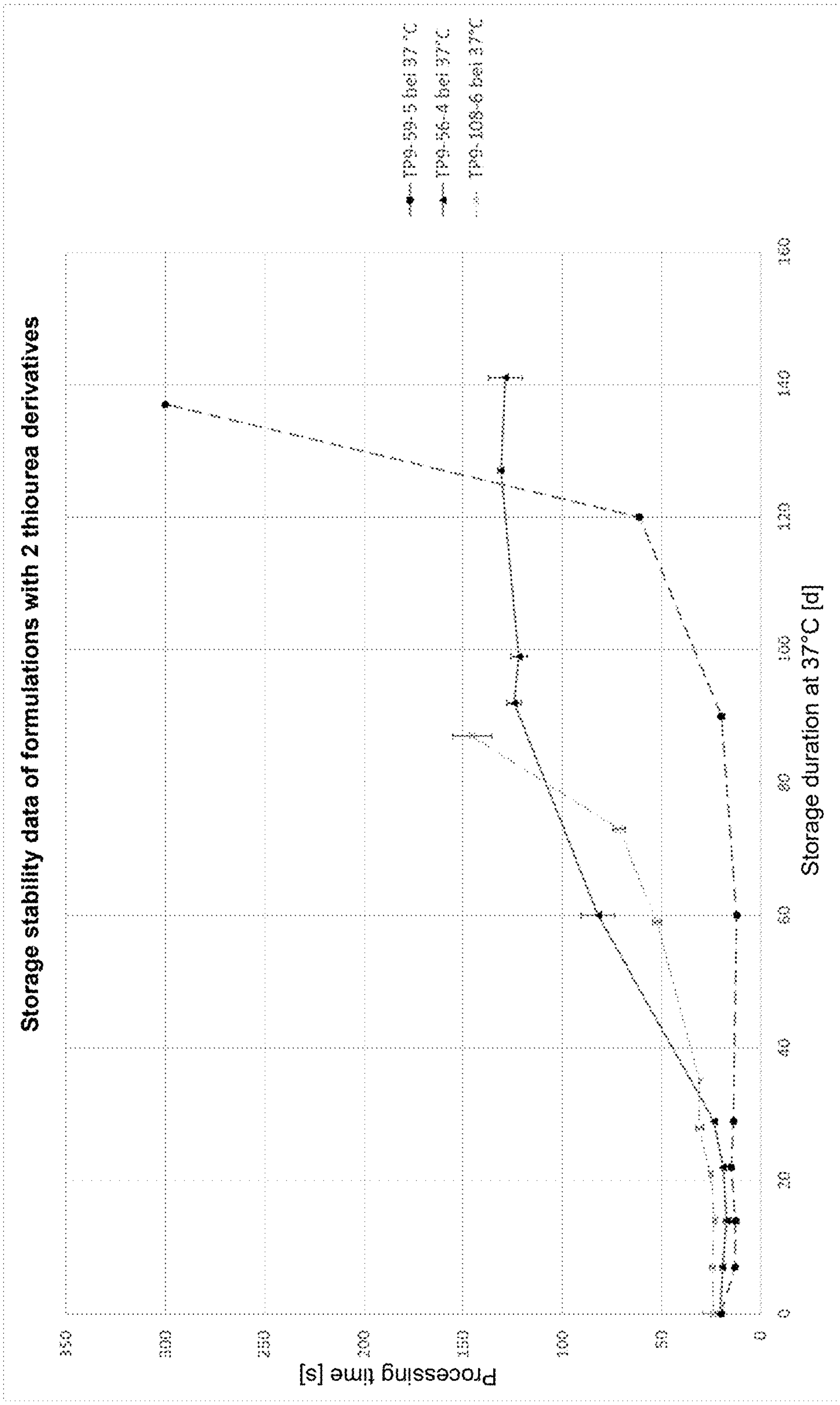
FIG. 1 shows storage stability of pastes with two different thiourea derivatives.

The dental materials according to the invention preferably contain at least one cyclic thiourea derivative and at least one acyclic thiourea derivative. It was found that the cyclic thiourea derivatives used according to the invention have a relatively high reactivity and bring about a rapid start of the polymerization. However, the polymerization stops quickly. In contrast, acyclic thiourea derivatives react more slowly, but it has been found that they are active for longer. By combining quick-reacting thiourea derivatives with slow-reacting thiourea derivatives, on the one hand a rapid start of the reaction can be brought about and on the other hand it can be ensured that the materials fully harden completely and have good mechanical properties after hardening.

The rapid start of the reaction makes it possible to remove the material from the patient's mouth quickly and thus to keep the stress for the patient low. As the impression tray has to be held manually during hardening, the effort for the staff carrying out the treatment is also considerably reduced. Once the polymerization initiated by the cyclic thiourea derivative has subsided, the material is not completely fully hardened and is in an elastic state, which makes an easy post-processing possible, e.g. by trimming or grinding. As the final hardening initiated by the acyclic thiourea derivative proceeds much more slowly, the elastic phase is, in comparison with conventional materials, significantly lengthened, which makes the post-processing of the restoration much easier.

It was found not only that a long elastic phase is obtained by combining differently reactive thiourea derivatives. It was particularly astonishing that the storage stability can be substantially improved by the addition of a third thiourea derivative.

By cyclic thiourea derivatives is here meant those compounds in which the nitrogen atoms of the thiourea group, together with the carbon atom lying in between and further carbon atoms, form a heterocyclic ring system. Cyclic thiourea derivatives of Formula (I):

Formula I

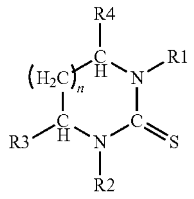

in which:

$R^1$, $R^2$ in each case are H or a $C_1$-$C_4$ alkyl radical, wherein at least one of these radicals is H;

$R^3$, $R^4$ independently of each other in each case are H, a $C_1$-$C_4$ alkyl radical or a $C_1$-$C_4$ alkoxy radical or, together with the carbon atoms to which they are bonded and the carbon atom lying in between, form a six-membered, carbocyclic, aliphatic or aromatic ring, which can be substituted by one or more, preferably 1 or 2, $C_1$-$C_4$ alkyl radicals and/or $C_1$-$C_4$ alkoxy radicals;

n is 0, 1, 2 or 3, preferably 0 or 1;

are preferred.

The variables of Formula I preferably have the following meanings:

$R^1$, $R^2$ in each case H or a $C_1$-$C_2$ alkyl radical, preferably H or methyl, wherein at least one of these radicals is H;

$R^3$, $R^4$ in each case H, a $C_1$-$C_2$ alkyl radical, preferably methyl, a $C_1$-$C_2$ alkoxy radical, preferably methoxy, or, together with the carbon atoms to which they are bonded and the carbon atom lying in between, form a benzene ring which can be substituted by a $C_1$-$C_2$ alkyl radical, preferably methyl, or a $C_1$-$C_2$ alkoxy radical, preferably methoxy;

n 0 or 1.

The variables of Formula I particularly preferably have the following meanings:

$R^1$, $R^2$ in each case H or methyl, wherein at least one of these radicals is H;

$R^3$, $R^4$ in each case H, a $C_1$-$C_2$ alkyl radical, preferably methyl, or a $C_1$-$C_2$ alkoxy radical, preferably methoxy, and n 1, or $R^1$, $R^2$ in each case H or methyl, wherein at least one of these radicals is H;

$R^3$, $R^4$, together with the carbon atoms to which they are bonded and the carbon atom lying in between, form a benzene ring which can be substituted by a $C_1$-$C_2$ alkyl radical, preferably methyl, or a $C_1$-$C_2$ alkoxy radical, preferably methoxy, and n 0.

In all cases, Formula I also comprises the corresponding isothiourea derivatives.

3,4,5,6-Tetrahydro-2-pyrimidinethiol (1), 2-imidazolidinethione (2), 2-mercaptobenzimidazole (4), 1-methyl-1H-benzimidazole-2-thiol and 2-mercapto-5-methoxybenzimidazole are particularly preferred.

(1)

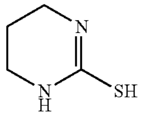

(2)

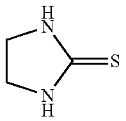

(4)

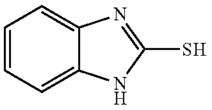

By acyclic thiourea derivatives is here meant those compounds in which the nitrogen atoms of the thiourea group are not incorporated into a ring system. However, acyclic thiourea derivatives can nevertheless contain cyclic groups.

Acyclic thiourea derivatives of Formula (II)

Formula II

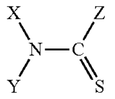

in which

X is H or Y,

Y is an alkyl radical with 1 to 8 carbon atoms, a cycloalkyl radical with 5 or 6 carbon atoms, a chlorine-, hydroxy- or mercapto-substituted alkyl radical with 1 to 8 carbon atoms, an alkenyl radical with 3 to 4 carbon atoms, an aryl radical with 6 to 8 carbon atoms, a chlorine-, hydroxy-, methoxy- or sulfonyl-substituted phenyl radical, an acyl radical with 2 to 8 carbon atoms, a chlorine- or methoxy-substituted acyl radical, an aralkyl radical with 7 to 8 carbon atoms or a chlorine- or methoxy-substituted aralkyl radical, and Z is $NH_2$, NHX or $NX_2$, are preferred.

Further preferred thiourea derivatives are the compounds listed in paragraph [0009] in EP 1 754 465 A1.

Acyclic thiourea derivatives of Formula (III):

Formula III

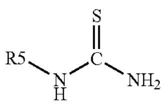

in which $R^5$ is a $C_1$-$C_{12}$ alkyl radical, preferably a $C_2$-$C_{10}$ alkyl radical, particularly preferably a $C_3$-$C_8$ alkyl radical and quite particularly preferably a $C_4$-$C_6$ alkyl radical, a $C_1$-$C_{12}$ alkene radical, preferably a $C_2$-$C_{10}$ alkene radical, particularly preferably a $C_3$-$C_8$ alkene radical and quite particularly preferably a $C_4$-$C_6$ alkene radical, a $C_1$-$C_{12}$ acyl radical, preferably a $C_2$-$C_{10}$ acyl radical, particularly preferably a $C_3$-$C_8$ acyl radical and quite particularly preferably a $C_4$-$C_6$ acyl radical, a pyridyl or phenyl radical, are particularly preferred.

Quite particularly preferred acyclic thiourea derivatives are acetyl, allyl, pyridyl and phenyl thiourea, hexanoyl thiourea (3) and mixtures thereof. Hexanoyl thiourea (3) is most preferred.

(3)

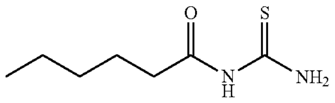

The compositions according to the invention contain at least 3, preferably 3 to 6, particularly preferably 3 or 4 and quite particularly preferably 3 different thiourea derivatives. The compositions can contain several acyclic and one or more cyclic thiourea derivatives or preferably several cyclic and one or more acyclic thiourea derivatives. Compositions which contain two to four, preferably two cyclic and one acyclic thiourea derivative are preferred.

Combinations which contain hexanoyl thiourea as acyclic thiourea derivative and at least two, preferably precisely two, cyclic thiourea derivatives are preferred. Compositions which contain hexanoyl thiourea, 2-mercaptobenzimidazole or 2-imidazolinethione and at least one, preferably precisely one (1), further cyclic thiourea derivative are particularly preferred. Compositions which contain hexanoyl thiourea, 2-mercaptobenzimidazole or 2-imidazolinethione and 3,4,5,6-tetrahydro-2-pyrimidinethiol are quite particularly preferred. A particularly preferred combination of three thiourea derivatives is a mixture of 3,4,5,6-tetrahydro-2-pyrimidinethiol (1), 2-imidazolidinethione (2) and hexanoyl thiourea (3).

Hydroperoxides preferred according to the invention are compounds of the formula $R^6$—$(OOH)_m$, in which $R^6$ is an aliphatic or aromatic hydrocarbon radical and m is 1 or 2. Preferred radicals R are alkyl and aryl groups. The alkyl groups can be straight-chain, branched or cyclic. Cyclic alkyl radicals can be substituted by aliphatic alkyl groups. Alkyl groups with 4 to 10 carbon atoms are preferred. Aryl groups can be unsubstituted or substituted by alkyl groups. Preferred aromatic hydrocarbon radicals are benzene radicals which are substituted with 1 or 2 alkyl groups. The aromatic hydrocarbon radicals preferably contain 6 to 12 carbon atoms. Particularly preferred hydroperoxides are t-amyl hydroperoxide, 1,1,3,3-tetramethylbutyl hydroperoxide, t-butyl hydroperoxide, t-hexyl peroxide, 2,5-dimethyl-2,5-di(hydroperoxy)hexane, diisopropylbenzene monohydroperoxide (DIHP), paramenthane hydroperoxide, p-isopropylcumene hydroperoxide and mixtures thereof. DIHP and cumene hydroperoxide (CHP) are quite particularly preferred.

Moreover, hydroperoxides according to the following Formula (IV),

Formula IV

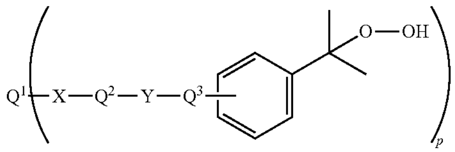

in which the variables have the following meanings:

$Q^1$ an p-valent, aromatic, aliphatic, linear or branched $C_1$-$C_{14}$ hydrocarbon radical, which can be interrupted by one or more S and/or O atoms and which can be unsubstituted or substituted by one or more substituents which are preferably selected from —OH, —$OR^7$, —Cl and —Br, wherein $R^7$ is an aliphatic, linear or branched $C_1$-$C_{10}$ hydrocarbon radical, X, Y independently of each other is in each case absent, —O—, —COO—; —$CONR^8$—, or —O—CO—$NR^9$—, wherein $R^8$ and $R^9$ independently of each other represent H or a $C_1$-$C_5$-alkyl radical, preferably H, methyl and/or ethyl, particularly preferably H, and wherein X and Y are preferably not absent at the same time, $Q^2$ is absent, an aliphatic, linear or branched $C_1$-$C_{14}$ alkylene radical, which can be interrupted by S and/or O atoms and which can be unsubstituted or substituted by —OH, —$OR^{10}$, —Cl and/or —Br, wherein $R^{10}$ is an aliphatic, linear or branched $C_1$-$C_{10}$ hydrocarbon radical, $Q^3$ a $C_1$-$C_3$ alkylene group or is absent, preferably —$CH_2$— or is absent, wherein X and/or Y is absent if $Q^2$ is absent, p 1, 2, 3 or 4, and wherein the substitution on the aromatic compound takes place in position 2, 3 or 4, relative to the cumene hydroperoxide group, are preferred according to the invention.

The variables preferably have the following meanings:

$Q^1$ a mono- or divalent, aliphatic, linear or branched $C_1$-$C_{10}$ hydrocarbon radical, which can be interrupted by one or more O atoms, preferably one O atom, and which can be substituted by one or more, preferably one, substituents which are selected from —OH and —$OR^7$ or is preferably unsubstituted, wherein $R^7$ is an aliphatic, linear or branched $C_1$-$C_6$ hydrocarbon radical, X, Y independently of each other is in each case absent, —O—, —COO— or —O—CO—$NR^9$—, wherein $R^9$ represents H or a $C_1$-$C_5$ alkyl radical, preferably H, methyl and/or ethyl and quite particularly preferably H, and wherein X and Y are preferably not absent at the same time, $Q^2$ is absent, a linear or branched $C_1$-$C_{10}$ alkylene radical, which can be interrupted by one or more O atoms, preferably one O atom, and which can be substituted by one or more, preferably one, substituents which are selected from —OH and —$OR^{10}$ or is preferably unsubstituted, wherein $R^{10}$ is an aliphatic, linear or branched $C_1$-$C_6$ hydrocarbon radical, p 1 or 2, and wherein the substitution on the aromatic compound takes place in position 3, preferably in position 4.

The variables particularly preferably have the following meanings:

$Q^1$ a mono- or divalent, aliphatic, linear or branched $C_1$-$C_5$ hydrocarbon radical, which can be interrupted by one O atom and which can be substituted by one OH group,

X —COO—,

Y is absent, $Q^2$ is absent or a linear $C_1$-$C_3$ alkylene radical, p 1 or 2, and wherein the substitution on the aromatic compound takes place in position 4.

The variables quite particularly preferably have the following meanings:

$Q^1$ a mono- or divalent, aliphatic, branched, preferably linear $C_1$-$C_4$ hydrocarbon radical,

X —COO—,

Y is absent, $Q^2$ is absent or a methylene radical, p 1 or 2, and wherein the substitution on the aromatic compound takes place in position 4.

Hydroperoxides of Formula (IV) and the preparation thereof are described in more detail in EP 3 692 976 A1. They are characterized in particular by the fact that they do not have an unpleasant odour. A quite particularly preferred hydroperoxide of Formula (IV) is 4-(2-hydroperoxypropan-2-yl)phenyl propionate (K220):

K220

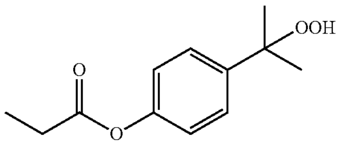

The hydroperoxides specifically named in paragraph [0025] of EP 3 692 976 A1 are further preferred.

According to a preferred embodiment, the materials according to the invention additionally contain a transition metal compound.

Transition metal compounds preferred according to the invention are compounds which are derived from transition metals which have at least two stable oxidation states. Compounds of the elements copper, iron, cobalt, nickel and manganese are particularly preferred. These metals have the following stable oxidation states: Cu(I)/Cu(II), Fe(II)/Fe (III), Co(II)/Co(III), Ni(II)/Ni(III), Mn(II)/Mn(III). Materials which contain at least one copper compound are particularly preferred.

The transition metals are preferably used in the form of their salts. Preferred salts are the nitrates, acetates, 2-ethylhexanoates and halides, wherein chlorides are particularly preferred.

The transition metals can furthermore advantageously be used in complexed form, wherein complexes with chelate-forming ligands are particularly preferred. Preferred simple ligands for complexing the transition metals are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N",N"-pentamethyldiethylenetriamine (PMDETA), tris[2-(dimethylamino)ethyl]amine ($Me_6TREN$), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl) ethylenediamine (TPEN), N,N-bis(2-pyridylmethyl)amine (BPMA), N,N-bis(2-pyridylmethyl)octylamine (BPMOA), 2,2'-bipyridine and 8-hydroxyquinoline. Quite particularly preferred ligands are acetylacetone, dimethylglyoxime and 1,10-phenanthroline.

In the case of electrically neutral ligands, the charge of the transition metal ions must be balanced by suitable counterions. For this, the above-named ions which are used to form salts are preferred, wherein acetates and chlorides are particularly preferred. Chlorides and complexes are characterized by a relatively good solubility in monomers, which are used to prepare dental materials.

Instead of the transition metal complexes, non-complex salts of the transition metals in combination with complex-forming organic compounds can be used to prepare the dental materials, preferred are the above-named chelate-forming compounds. The organic ligands form the catalytically active complexes when mixed with the transition metal salts. The use of such combinations of transition metal salts and organic ligands is preferred.

Transition metal compounds of the metals copper, iron, cobalt and nickel are preferred.

Preferred copper salts are Cu(II) carboxylates (e.g. of acetic acid or 2-ethylhexanoic acid), $CuCl_2$, $CuBr_2$, $CuI_2$, particularly preferably CuBr and quite particularly preferably CuCl. Preferred copper complexes are complexes with the ligands acetylacetone, phenanthroline (e.g. 1,10-phenanthroline (phen)), the aliphatic amines, such as e.g. 1,1,4,7,10,10-hexamethyltriethylenetetramine (HMTETA), N, N, N',N",N"-pentamethyldiethylenetriamine (PMDETA), tris[2-(dimethylamino)ethyl]amine ($Me_6TREN$).

Preferred iron salts are $FeCl_3$, $FeBr_2$ and $FeCl_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (Prilm). The complexes $Fe(acac)_2$ and $FeCl_2(PPh_3)_2$ are quite particularly preferred.

Preferred nickel salts are $NiBr_2$ and $NiCl_2$, preferred nickel complexes are nickel acetylacetonate and $NiBr_2(PPh_3)_2$.

According to the invention, copper compounds, copper complexes and in particular mixtures of copper salts and complexing organic ligands are particularly preferred. Salts and complexes of monovalent copper ($Cu^+$) are quite particularly preferred, copper(I) chloride (CuCl) is most preferred. Compositions which contain a salt of monovalent copper and in particular CuCl are characterized by a particularly good storage stability.

The initiator system according to the invention is particularly suitable for curing radically polymerizable compositions.

Compositions according to the invention preferably contain at least one radically polymerizable monomer in addition to the initiator system. Compositions which contain at least one mono- or multifunctional (meth)acrylate as radically polymerizable monomer are particularly preferred. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which are to be hardened intraorally preferably contain mono- and/or multifunctional methacrylates as radically polymerizable monomer.

Preferred mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)phenyl] propane) (SR-348c, from Sartomer; comprises 3 ethoxy groups) and 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with mol $\alpha,\alpha,\alpha',\alpha'$-tetramethyl-m-xylylene diisocyanate), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate ($D_3MA$), bis(methacryloyloxymethyl)tricyclo-[5.2.1.02,6]decane (DCP), polyethylene glycol or polypropylene glycol dimethacrylates, such as e.g. polyethylene glycol 200 dimethacrylate or polyethylene glycol 400 dimethacrylate (PEG 200 DMA or PEG 400 DMA) or 1,12-dodecanediol dimethacrylate, or a mixture thereof.

The compositions according to the invention can advantageously additionally contain an initiator for the radical photopolymerization in addition to the initiator system according to the invention. Such compositions are dual-curing, i.e. they can be cured both chemically and by light. Preferred photoinitiators are benzophenone, benzoin as well as their derivatives, $\alpha$-diketones and their derivatives, such as 9,10-phenanthrenequinone, 1-phenyl-propane-1,2-dione, diacetyl and 4,4'-dichlorobenzil. Camphorquinone (CQ) and 2,2-dimethoxy-2-phenyl-acetophenone are preferably used in combination with amines as reducing agent, such as e.g. 4-(dimethylamino)-benzoic acid ethyl ester (EDMAB), or N,N-dimethylaminoethyl methacrylate.

Those compositions which do not contain amines are preferred according to the invention. Norrish type I photoinitiators are therefore particularly preferred. Norrish type I photoinitiators do not require an amine component.

Preferred Norrish type I photoinitiators are acyl- or bisacylphosphine oxides. Monoacyltrialkylgermane, diacyldialkylgermane and tetraacylgermane compounds, such as e.g. benzoyltrimethylgermane, dibenzoyldiethylgermane, bis(4-methoxybenzoyl)diethylgermane (Ivocerin®), tetrabenzoylgermane and tetrakis(o-methylbenzoyl)germane are particularly preferred. Moreover, mixtures of the different photoinitiators can be used, such as e.g. bis(4-methoxybenzoyl)diethylgermane or tetrakis(o-methyl benzoyl)germane in combination with camphorquinone and 4-dimethylaminobenzoic acid ethyl ester.

The compositions according to the invention can moreover advantageously contain one or more organic or inorganic fillers. Particulate fillers are preferred. Filler-containing compositions are particularly suitable as dental fixing cements or filling composites as well as for the production of temporary crowns and bridges.

Preferred inorganic fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as pyrogenic silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V)

oxide, barium sulfate or mixed oxides of $SiO_2$ with ytterbium(III) oxide or tantalum(V) oxide. The dental materials according to the invention can furthermore contain fibrous fillers, nanofibres, whiskers or mixtures thereof.

Preferably the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, glass powders with a particle size of from 0.2 to 1.5 μm, in particular radiopaque glass powders of e.g. barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

Moreover, ground prepolymers or pearl polymers (isofillers) are suitable as filler. These can consist exclusively of organic polymers, or organic polymers which themselves are filled with inorganic fillers such as radiopaque glass powder (s) and ytterbium trifluoride. The above-defined monomers and fillers are suitable for the preparation of the ground prepolymers and pearl polymers. Compositions for the production of full dentures preferably contain exclusively organic fillers, particularly preferably ground polymers or pearl polymers based on polymethyl methacrylate (PMMA), quite particularly preferably pearl polymers based on PMMA, as fillers.

Unless otherwise stated, all particle sizes are weight-average particle sizes, wherein the particle-size determination in the range of from 0.1 μm to 1000 μm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 μm are preferably determined by means of dynamic light scattering (DLS). The measurement of the particle size in the range of from 5 nm to 0.1 μm is preferably effected by dynamic light scattering (DLS) of aqueous particle dispersions, preferably with a Malvern Zetasizer Nano ZS (Malvern Instruments, Malvern UK) with an He—Ne laser with a wavelength of 633 nm, at a scattering angle of 90° at 25° C.

Particle sizes smaller than 0.1 μm can also be determined by means of SEM or TEM spectroscopy. The transmission electron microscopy (TEM) is preferably carried out with a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The light scattering decreases as the particle size decreases, but fillers with a small particle size have a greater thickening action. The fillers are divided according to their particle size into macrofillers and microfillers, wherein fillers with an average particle size of from 0.2 to 10 μm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splintery parts. Microfillers such as mixed oxides can be prepared e.g. by hydrolytic co-condensation of metal alkoxides.

To improve the bond between the filler particles and the crosslinked polymerization matrix, the fillers are preferably surface-modified, particularly preferably by silanization, quite particularly preferably by radically polymerizable silanes, in particular with 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxydecyl dihydrogen phosphate can also be used.

Moreover, the compositions according to the invention can contain one or more further additives, above all stabilizers, colorants, microbiocidal active ingredients, fluoride-ion-releasing additives, foaming agents, optical brighteners, plasticizers and/or UV absorbers.

The materials according to the invention preferably comprise two physically separated components which are mixed with each other for use. The first component (catalyst paste) comprises the hydroperoxide or hydroperoxides, and the second component (base paste) comprises the thiourea derivatives and optionally the transition metal compound. Base paste and catalyst paste are preferably mixed with each other in a volume ratio of 1:1. The hardening reaction is initiated by mixing base and catalyst pastes.

The base paste preferably comprises 0.07 to 3.50 wt.-%, particularly preferably 0.07 to 3.3 wt.-%, quite particularly preferably 0.20 to 2.50 wt.-% and most preferably 0.35 to 2.10 wt.-% of at least one cyclic thiourea derivative and 0.04 to 2.3 wt.-%, particularly preferably 0.04 to 2.00 wt.-%, particularly preferably 0.10 to 1.5 wt.-% and most preferably 0.20 to 1.2 wt.-% of at least one acyclic thiourea derivative.

According to a preferred embodiment, the base paste comprises 0.03 to 2.50 wt.-%, particularly preferably 0.10 to 2.00 wt.-% and most preferably 0.15 to 1.50 wt.-% 3,4,5,6-tetrahydro-2-pyrimidinethiol and/or 0.04 to 1.30 wt.-%, particularly preferably 0.10 to 1.00 wt.-% and most preferably 0.15 to 0.60 wt.-% 2-mercaptobenzimidazole and/or 0.04 to 2.00 wt.-%, particularly preferably 0.10 to 1.50 wt.-% and most preferably 0.25 to 1.20 wt.-% hexanoyl thiourea, wherein materials which contain all three named cyclic thiourea derivatives in each case in the listed quantities are particularly advantageous.

The quantities of the individual thiourea derivatives are preferably chosen here such that the weight ratio of 3,4,5,6-tetrahydro-2-pyrimidinethiol to 2-mercaptobenzimidazole lies in a range of from 0.15 to 4.00, particularly preferably 0.20 to 3.50 and most preferably 0.25 to 3.00. The weight ratio of 3,4,5,6-tetrahydro-2-pyrimidinethiol to hexanoyl thiourea preferably lies in a range of from 0.04 to 3.50, particularly preferably 0.40 to 3.00 and most preferably 0.60 to 2.70. The weight ratio of 2-mercaptobenzimidazole to hexanoyl thiourea preferably lies in a range of from 0.05 to 2.50, particularly preferably 0.10 to 1.2 and most preferably 0.20 to 0.90.

The base paste preferably comprises a total of 0.10 to 4.00 wt.-%, particularly preferably 0.50 to 2.50 wt.-% and most preferably 1.00 to 2.00 wt.-% of thiourea derivatives.

The thiourea derivatives are preferably used in a total molar quantity of from 50 to 400 mol-%, preferably 75 to 300 mol-% and quite particularly preferably 100 to 200 mol-%, relative to the molar quantity of hydroperoxide in the catalyst paste.

Preferably the base paste additionally comprises 0.0001 to 1 wt.-%, preferably 0.0005 to 0.500 wt.-% and particularly preferably 0.0007 to 0.020 wt.-% of one or more transition metal compounds. The total mass of transition metal compounds relative to the mass of the base paste is specified.

The base paste preferably has the following composition:

0.10 to 5.00 wt.-%, preferably 0.50 to 4.00 wt.-%, particularly preferably 1.00 to 2.00 wt.-% thiourea derivatives, 0.0001 to 1 wt.-%, preferably 0.0005 to 0.5 wt.-%, particularly preferably 0.0007 to 0.02 wt.-% of at least one transition metal compound, 5 to 95 wt.-%, preferably 10 to 95 wt.-% and particularly preferably 10 to 90 wt.-% of at least one radically polymerizable monomer, 0 to 85 wt.-% of at least one filler, and optionally 0.01 to 5 wt.-%, preferably 0.1 to 3 wt.-% and particularly preferably 0.1 to 2 wt.-% of one or more additives.

The above data in all cases relate to the mass of the base paste.

The catalyst paste preferably comprises one or more hydroperoxides, preferably in a total quantity of from 0.01 to 5.0 wt.-%, particularly preferably 0.05 to 4.0 wt.-% and quite particularly preferably 0.1 to 3.75 wt.-%, relative to the mass of the catalyst paste.

The catalyst paste preferably has the following composition:

0.01 to 6 wt.-%, preferably 0.05 to 5.0 wt.-% and particularly preferably 0.1 to 4.0 wt.-% of at least one hydroperoxide, preferably CHP and/or K220, 5 to 95 wt.-%, preferably 10 to 95 wt.-% and particularly preferably 10 to 90 wt.-% of at least one radically polymerizable monomer, 0 to 85 wt.-% of at least one filler, and optionally 0.01 to 5 wt.-%, preferably 0.1 to 3 wt.-% and particularly preferably 0.1 to 2 wt.-% of one or more additives, in each case relative to the mass of the catalyst paste.

After mixing catalyst and base pastes, the materials according to the invention preferably have the following overall composition:

(a) 0.005 to 3 wt.-%, preferably 0.025 to 2.5 wt.-% and particularly preferably 0.05 to 2.0 wt.-% of at least one hydroperoxide, preferably CHP and/or K220, (b) 0.005 to 3.0 wt.-%, preferably 0.015 to 2.125 wt.-%, particularly preferably 0.025 to 1.5 wt.-% thiourea derivatives, (c) 0.00005 to 0.5 wt.-%, preferably 0.00025 to 0.25 wt.-%, particularly preferably 0.00035 to 0.01 wt.-% of at least one transition metal compound, (d) 5 to 95 wt.-%, preferably 10 to 95 wt.-% and particularly preferably 10 to 90 wt.-% of at least one radically polymerizable monomer, (e) 0 to 85 wt.-% of at least one filler, and (f) optionally 0.01 to 5 wt.-%, preferably 0.1 to 3 wt.-% and particularly preferably 0.1 to 2 wt.-% of one or more additives, in each case relative to the total mass of the composition.

The filler content is geared towards the desired intended use of the material. Filling composites preferably have a filler content of from 50 to 85 wt.-%, particularly preferably 70 to 80 wt.-%. Materials for the production of temporary crowns and bridges preferably have a filler content of from 40 to 70 wt.-%, particularly preferably 45 to 60 wt.-%, and dental cements preferably have a filler content of from 10 to 70 wt.-%, particularly preferably 60 to 70 wt.-%. The data relate to the total mass of the material.

Those compositions which consist of the named substances are particularly preferred. Furthermore, those compositions in which the individual components are in each case selected from the above-named preferred and particularly preferred substances are preferred. In all cases, an individual component or a mixture of several components can be used in each case, for example a mixture of monomers.

The compositions according to the invention are particularly suitable as dental materials, in particular as dental cements, filling composites and veneering materials as well as materials for the production of prostheses, artificial teeth, inlays, onlays, crowns and bridges, quite particularly for the production of temporary crowns and bridges. The compositions are suitable for intraoral application by the dentist for the restoration of damaged teeth, i.e. for therapeutic application, e.g. as dental cements, filling composites and veneering materials. However, they can also be used non-therapeutically (extraorally), for example in the production or repair of dental restorations, such as prostheses, artificial teeth, inlays, onlays, crowns and bridges.

The compositions according to the invention are moreover suitable for the production of shaped bodies for dental, but also for non-dental purposes, which can be produced e.g. by means of casting, compression moulding and in particular by additive processes such as 3D printing.

For the production of temporary crowns and bridges, first of all an impression of the tooth or teeth to be treated is made. Then the tooth or teeth are ground and the impression is then filled with a self-curing restoration material. The blended material is applied from a mixing tip using light pressure directly into the impression or the deep-drawing film. During the infilling, the tip should be immersed in the material in order to achieve a bubble-free filling of the impression. If necessary, the prepared teeth can be surrounded with the restoration material for the bubble-free formation of the preparation margin.

The impression filled with the material is then pressed onto the prepared teeth. After approximately 1 to 2 minutes the material is in a hard-elastic partially hardened state and can be removed from the mouth together with the impression.

After the temporary plastic prosthesis has been removed from the anatomical impression or possibly from the core, excess material is removed after further curing (approx. 4 to 5 minutes) using rotating instruments, e.g. using a cross-cut tungsten carbide bur, or using a scalpel. The inhibition layer is preferably removed with alcohol or by polishing. The restoration is then left to cure completely.

The invention is explained in more detail in the following with reference to embodiment examples and figures.

FIG. 1 shows the storage stability of pastes with two different thiourea derivatives. The processing time of the pastes increases with the storage duration, which is an indication of instability. The pastes are stable for approx. three months at 37° C.

Figure 2:
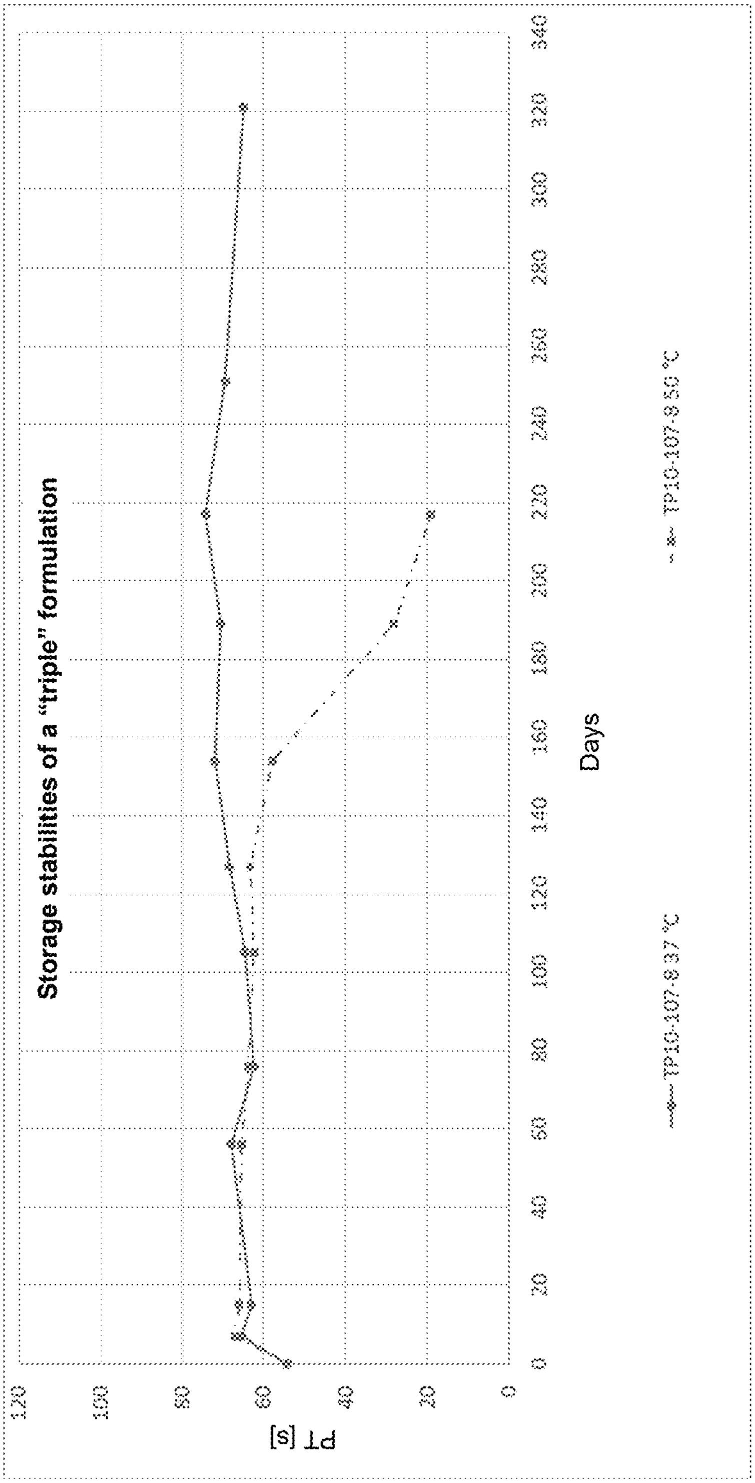
FIG. 2 shows storage stability of pastes with three different thiourea derivatives.

FIG. 2 shows the storage stability of pastes with three different thiourea derivatives. The pastes are stable for 5 months even at 50° C. Only after that can a decrease in the processing time be seen.

Embodiment Examples

The following materials are used in the embodiment examples:

DCP bis(methacryloyloxymethyl)tricyclo-[5.2.1.02,6]-decane (CAS No. 43048-08-4)

RM3 UDMA (CAS No. 72869-86-4)

SR348C 2-[4-(2-methacryloyloxyethoxyethoxy)-phenyl]-2-[4-(2-methacryloyloxyethoxy)-phenyl]-propane) (SR-348c, from Sartomer; comprises 3 ethoxy groups; CAS No. 41637-38-1)

CHP cumene hydroperoxide (CAS No. 80-15-9)

K220 4-(2-hydroperoxypropan-2-yl)phenyl propionate (CAS No. 2515246-70-3)

2-MBI 2-mercaptobenzimidazole (CAS No. 583-39-1)

1-methyl-MBI 1-methyl-1H-benzimidazole-2-thiol (CAS No. 2360-22-7)

THPT 3,4,5,6-tetrahydro-2-pyrimidinethiol (CAS No. 2055-46-1)

K107 hexanoyl thiourea (CAS No. 41510-13-8)

CuCl copper(I) chloride (CAS No. 7758-89-6)

HDK2000 pyrogenic silica treated with trimethylsilane, BET surface area approx. 200 $m^2/g$ (Wacker Chemie AG)

SG-SO100NCM P8 $SiO_2$ coated with methacryloxypropyltrimethoxysilane (CAS No. 7631-86-9)

BHT butylhydroxytoluene (CAS No. 128-37-0)

Optamint® flavour (from Symrise AG)

Example 1

Determining the Influence of the Number of Thiourea Derivatives on the Storage Stability The materials listed in Table 1 were prepared by homogeneous mixing of the components named in the table. In each case a base paste (Base) and a catalyst paste (Cat) were prepared. To prepare the pastes, the respective initiator constituents and additives were added to the monomer and the mixture was then stirred for several hours until the solids had completely dissolved. After that the fillers were added and homogeneously blended in a centrifugal mixer (SpeedMixer®, from Hauschild). After the pastes had been vacuumized, they were separately poured into a double-push syringe. Then base and catalyst pastes were blended with each other, in each case in the volume ratio 1:1, and the processing time (PT) was measured according to the EN ISO-4049 standard. To determine the mechanical properties of the materials, test pieces were produced and their flexural strength and flexural modulus of elasticity were determined according to the EN ISO-4049 standard (Dentistry—Polymer-based filling, restorative and luting materials). To determine the length of the elastic phase, catalyst and base pastes were blended in a volume ratio 1:1. After the hardening had begun (established by pressing on the test piece), the stopwatch was started, and when the test piece could no longer be cut using a scalpel it was stopped. The results are specified in Table 3.

To determine the storage stability, the pastes were stored for five months at 37° C. or 50° C. The processing time was measured periodically. The results are reproduced in FIGS. 1 and 2. FIG. 1 shows the storage stability of pastes with two different thiourea derivatives and FIG. 2 shows the storage stability of pastes with three different thiourea derivatives. FIG. 1 shows that the processing time of the pastes increases with the storage duration, which is an indication of instability. The pastes with two different thiourea derivatives were stable for approx. three months at 37° C. FIG. 2 shows that pastes with three different thiourea derivatives were stable for 5 months even at 50° C.

TABLE 1

Composition of the catalyst and base pastes (data in wt.-%)

| Component | | TP9-59-5*) | | TP9-56-4*) | | TP9-108-6*) | | TP10-107-8 | |
|---|---|---|---|---|---|---|---|---|---|
| | | Base | Cat | Base | Cat | Base | Cat | Base | Cat |
| Monomer | SR348C | 47.07 | 46.02 | 47.04 | 46.47 | 18.98 | 18.53 | 23.43 | 22.83 |
| | RM3 | | | | | 23.72 | 23.23 | 17.92 | 17.87 |
| | DCP | | | | | 4.75 | 4.65 | 5.12 | 4.84 |
| Peroxide | CHP | | 2.51 | | 2.49 | | 2.52 | | 2.41 |
| Thiourea | 2-MBI | 0.52 | | 0.50 | | 0.49 | | | |
| | K107 | 0.49 | | 0.49 | | 0.49 | | 0.48 | |
| | THPT | | | | | | | 0.24 | |
| | 2-imidazolidinethione | | | | | | | 0.14 | |
| Cu salt | CuCl | 0.02 | | 0.02 | | 0.02 | | 0.01 | |
| Flavour | Optamint ® | 0.49 | | 0.96 | | 0.50 | | 0.49 | |
| Stabilizer | BHT | 0.05 | 0.05 | 0.05 | 0.05 | 0.07 | 0.06 | 0.05 | 0.05 |
| Filler | HDK 2000 | 2.96 | 3.00 | 3.00 | 3.01 | 3.00 | 3.01 | 5.02 | 4.99 |
| | SG-SO100NCMP8 | 48.41 | 48.41 | 47.95 | 47.99 | 47.98 | 47.99 | 47.10 | 47.01 |
| Total | | 100.00 | 100.00 | 100.00 | 100.00 | 100.00 | 100.00 | 100.00 | 100.00 |

*)Comparison example

Example 2

Determining the Mechanical Properties of Restoration Materials

The materials described in Table 2 were prepared analogously to Example 1. The processing time, the length of the elastic phase and the mechanical properties were then determined in the way described in Example 1. The results are specified in Table 3. Materials No. 1 and No. 2 contain in each case only two thiourea derivatives. These materials have a good flexural strength, a good flexural modulus and a sufficiently long elastic phase. However, the processing time is relatively short and the storage stability is unsatisfactory (FIG. 1). The remaining materials contain in each case three different thiourea derivatives. These materials are characterized by an extended processing time with comparable mechanical properties and a comparable length of the elastic phase.

TABLE 2

Composition of the catalyst and base pastes (data in wt.-%)

| | | TP10-22-5 | | TP10-45-13 | | TP10-51-7 | | TP10-51-8 | | TP10-55-11 | | TP10-55-12 |
|---|---|---|---|---|---|---|---|---|---|---|---|---|
| | Component | Base | Cat | Base | Cat | Base | Cat | Base | Cat | Base | Cat | Base |
| Monomer | SR348C | 22.96 | 21.78 | 23.35 | 22.69 | 23.35 | 22.17 | 23.11 | 22.17 | 23.38 | 22.17 | 23.03 |
| | RM3 | 18.63 | 17.67 | 18.70 | 18.22 | 18.76 | 17.74 | 18.57 | 17.74 | 18.78 | 17.74 | 18.67 |
| | DCP | 4.73 | 4.48 | 4.66 | 4.64 | 4.77 | 4.44 | 4.72 | 4.44 | 4.78 | 4.44 | 4.66 |
| Peroxide | CHP | 0 | 0 | 0 | 2.40 | 0 | 3.60 | 0 | 3.60 | 0 | 3.60 | 0 |
| | K220 | 0 | 3.89 | 0 | 0 | 0 | 0 | 0 | 0 | 0 | 0 | 0 |
| Thiourea | 2-MBI | 0.25 | 0 | 0.41 | 0 | 0.41 | 0 | 0.41 | 0 | 0.21 | 0 | 0.83 |
| | THPT | 0 | 0 | 0.33 | 0 | 0.16 | 0 | 0.64 | 0 | 0.33 | 0 | 0.33 |
| | 2-imidazolidinethione | 0 | 0 | 0 | 0 | 0 | 0 | 0 | 0 | 0 | 0 | 0 |
| | 1-methyl-MBI | 0.24 | 0 | 0 | 0 | 0 | 0 | 0 | 0 | 0 | 0 | 0 |
| | K107 | 0.49 | 0 | 0.49 | 0 | 0.48 | 0 | 0.48 | 0 | 0.48 | 0 | 0.48 |
| Cu salt | CuCl | 0.01 | 0 | 0.01 | 0 | 0.01 | 0 | 0.01 | 0 | 0.01 | 0 | 0.01 |
| Stabilizer | BHT | 0.20 | 0.17 | 0.05 | 0.05 | 0.05 | 0.05 | 0.05 | 0.05 | 0.06 | 0.05 | 0.05 |
| Flavour | Optamint ® | 0.48 | 0 | 0 | 0 | 0 | 0 | 0 | 0 | 0 | 0 | 0 |
| Filler | HDK 2000 | 5.00 | 5.02 | 5.01 | 5.01 | 5.00 | 5.00 | 5.00 | 5.00 | 5.02 | 5.00 | 4.97 |
| | SG-SO100 NCMP8 | 47.01 | 46.99 | 46.98 | 47.00 | 47.00 | 47.00 | 47.00 | 47.00 | 46.96 | 47.00 | 46.97 |
| Total | | 100 | 100 | 100 | 100 | 100 | 100 | 100 | 100 | 100 | 100 | 100 |

| | | TP10-55-12 | TP10-25-7 | | TP10-25-8 | | TP10-25-9 | | TP10-25-10 | | TP10-25-11 | |
|---|---|---|---|---|---|---|---|---|---|---|---|---|
| | Component | Cat | Base | Cat | Base | Cat | Base | Cat | Base | Cat | Base | Cat |
| Monomer | SR348C | 22.17 | 23.52 | 22.76 | 23.24 | 22.76 | 23.83 | 22.76 | 23.76 | 22.76 | 23.91 | 22.76 |
| | RM3 | 17.74 | 18.82 | 18.21 | 18.82 | 18.21 | 18.45 | 18.21 | 18.74 | 18.21 | 18.26 | 18.21 |
| | DCP | 4.44 | 4.71 | 4.56 | 4.70 | 4.56 | 4.70 | 4.56 | 4.76 | 4.56 | 4.81 | 4.56 |
| Peroxide | CHP | 3.60 | 0 | 2.40 | 0 | 2.40 | 0 | 2.40 | 0 | 2.40 | 0 | 2.40 |
| | K220 | 0 | 0 | 0 | 0 | 0 | 0 | 0 | 0 | 0 | 0 | 0 |
| Thiourea | 2-MBI | 0 | 0 | 0 | 0 | 0 | 0 | 0 | 0 | 0 | 0.36 | 0 |
| | THPT | 0 | 0.24 | 0 | 0.35 | 0 | 0.35 | 0 | 0.25 | 0 | 0.29 | 0 |
| | 2-imidazolidinethione | 0 | 0.15 | 0 | 0.30 | 0 | 0.29 | 0 | 0.16 | 0 | 0 | 0 |
| | 1-methyl-MBI | 0 | 0 | 0 | 0 | 0 | 0 | 0 | 0 | 0 | 0 | 0 |
| | K107 | 0 | 0.48 | 0 | 0.48 | 0 | 0.27 | 0 | 0.25 | 0 | 0.29 | 0 |
| Cu salt | CuCl | 0 | 0.01 | 0 | 0.01 | 0 | 0.01 | 0 | 0.01 | 0 | 0.01 | 0 |
| Stabilizer | BHT | 0.05 | 0.08 | 0.05 | 0.09 | 0.05 | 0.07 | 0.05 | 0.05 | 0.05 | 0.06 | 0.05 |
| Flavour | Optamint ® | 0 | 0 | 0 | 0 | 0 | 0 | 0 | 0 | 0 | 0 | 0 |
| Filler | HDK 2000 | 5.00 | 5.00 | 5.01 | 5.00 | 5.01 | 5.00 | 5.01 | 5.01 | 5.01 | 4.99 | 5.01 |
| | SG-SO100 NCMP8 | 47.00 | 46.99 | 47.02 | 47.00 | 47.02 | 47.03 | 47.02 | 47.00 | 47.02 | 47.02 | 47.02 |
| Total | | 100 | 100 | 100 | 100 | 100 | 100 | 100 | 100 | 100 | 100 | 100 |

TABLE 3

| Properties of the materials | | | | | |
|---|---|---|---|---|---|
| No. | Material | PT [s] | Flexural strength [MPa] | Flexural modulus [MPa] | Length of the elastic phase [s] |
| 1 | TP9-59-5*) | 20 | 90 | 3858 | 80 |
| 2 | TP9-108-6*) | 24 | 95 | 4114 | 87 |
| 3 | TP10-22-5 | 35 | 76 | 2709 | 100 |
| 4 | TP10-25-7 | 47 | 128 | 4800 | 100 |
| 5 | TP10-25-8 | 52 | 117 | 4376 | 100 |
| 6 | TP10-25-9 | 56 | 110 | 4436 | 70 |
| 7 | TP10-25-10 | 52 | 97 | 4221 | 90 |
| 8 | TP10-25-11 | 56 | 83 | 3251 | 80 |
| 9 | TP10-45-13 | 71 | 83 | 3107 | 90 |
| 10 | TP10-51-7 | 66 | 91 | 4249 | 100 |
| 11 | TP10-51-8 | 53 | 90 | 4414 | 80 |
| 12 | TP10-55-11 | 53 | 97 | 4490 | 60 |
| 13 | TP10-55-12 | 42 | 95 | 4544 | 70 |

*)Comparison example from Example 1

The invention claimed is:

1. A radically polymerizable dental material, which comprises a combination of at least three different thiourea derivatives and at least one hydroperoxide as initiator system for the radical polymerization, wherein the at least three different thiourea derivatives comprise at least two cyclic and one acyclic thiourea derivatives, wherein the at least two cyclic thiourea derivatives are selected from the group consisting of 3,4,5,6-tetrahydro-2-pyrimidinethiol, 2-imidazolidinethione, 2-mercaptobenzimidazole, 1-methyl-1H-benzimidazole-2-thiol and 2-mercapto-5-methoxybenzimidazole, and wherein the one acyclic thiourea derivative is hexanoyl thiourea.

2. The dental material according to claim 1, wherein the at least one hydroperoxide is represented by the formula $R^6$—$(OOH)_m$, in which $R^6$ is an aliphatic or aromatic hydrocarbon radical and m is 1 or 2, and/or Formula (IV):

Formula IV

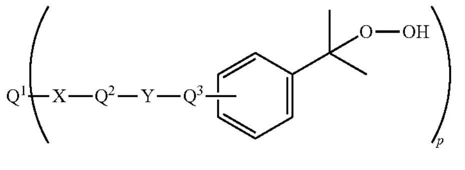

in which the variables have the following meanings:

$Q^1$ is a p-valent, aromatic, aliphatic, linear or branched $C_1$-$C_{14}$ hydrocarbon radical, which is optionally interrupted by one or more S and/or O atoms and which is unsubstituted or substituted by one or more substituents which are selected from —OH, —$OR^7$, —Cl and —Br, wherein $R^7$ is an aliphatic, linear or branched $C_1$-$C_{10}$ hydrocarbon radical;

X and Y independently of each other is in each case absent, —O—, —COO—; —$CONR^8$—, or —O—CO—$NR^9$—, wherein $R^8$ and $R^9$ independently of each other represent H or a $C_1$-$C_5$ alkyl radical;

$Q^2$ is absent, an aliphatic, linear or branched $C_1$-$C_{14}$ alkylene radical, which is optionally interrupted by S and/or O atoms and which is unsubstituted or substituted by —OH, —$OR^{10}$, —Cl and/or —Br, wherein $R^{10}$ is an aliphatic, linear or branched $C_1$-$C_{10}$ hydrocarbon radical;

$Q^3$ is a $C_1$-$C_3$ alkylene group or is absent, wherein X and/or Y is absent if $Q^2$ is absent;

p is 1, 2, 3 or 4; and wherein the substitution on the aromatic compound takes place in position 2, 3 or 4, relative to the cumene hydroperoxide group.

3. The dental material according to claim 2, wherein the at least one hydroperoxide is selected from the group consisting of t-amyl hydroperoxide, 1,1,3,3-tetramethylbutyl hydroperoxide, t-butyl hydroperoxide, t-hexyl peroxide, 2,5-dimethyl-2,5-di(hydroperoxy) hexane, diisopropylbenzene monohydroperoxide, paramenthane hydroperoxide, p-isopropylcumene hydroperoxide, 4-(2-hydroperoxypropan-2-yl)phenyl propionate and a mixture thereof.

4. The dental material according to claim 1, which additionally comprises a transition metal compound.

5. The dental material according to claim 1, which comprises two components, wherein the first component comprises 0.01 to 5 wt.-% or 0.05 to 4.0 wt.-% or 0.1 to 3.75 wt.-% of the at least one hydroperoxide, relative to the mass of the first component, and wherein the second component comprises 50 to 400 mol-% or 75 to 300 mol-% or 100 to 200 mol-% of the at least three thiourea derivatives, relative to the molar quantity of hydroperoxide in the first component.

6. The dental material according to claim 1, which additionally comprises at least one radically polymerizable monomer.

7. The dental material according to claim 6, wherein the at least one radically polymerizable monomer is selected from the group consisting of methyl (meth)acrylate, ethyl (meth)acrylate, 2-hydroxyethyl (meth)acrylate, butyl (meth) acrylate, benzyl (meth)acrylate, tetrahydrofurfuryl (meth) acrylate, isobornyl (meth)acrylate, p-cumylphenoxyethylene glycol methacrylate, 2-(2-biphenyloxy) ethyl methacrylate, bisphenol A dimethacrylate, an addition product of methacrylic acid and bisphenol A diglycidyl ether, ethoxylated bisphenol A dimethacrylate, propoxylated bisphenol A dimethacrylate, 2-[4-(2-methacryloyloxyethoxyethoxy)phenyl]-2-[4-(2-methacryloyloxyethoxy)phenyl] propane), 2,2-bis[4-(2-methacryloxypropoxy)-phenyl] propane, an addition product of 2-hydroxyethyl methacrylate and 2,2,4-trimethylhexamethylene-1,6-diisocyanate, an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate, diethylene glycol dimethacrylate, [−]triethylene glycol dimethacrylate, [−] tetraethylene glycol dimethacrylate, trimethylolpropane trimethacrylate, pentaerythritol tetramethacrylate, glycerol di-methacrylate, glycerol trimethacrylate, 1,4-butanediol dimethacrylate, 1,10-decanediol dimethacrylate ($D_3MA$), bis(methacryloyloxymethyl)tricyclo-[5.2.1.02,6]decane, a polyethylene glycol dimethacrylate, polypropylene glycol dimethacrylate, polyethylene glycol 200 dimethacrylate (PEG 200 DMA), polyethylene glycol 400 dimethacrylate (PEG 400 DMA), 1,12-dodecanediol dimethacrylate and a mixture thereof.

8. The dental material according to claim 1, which additionally comprises at least one organic filler, inorganic filler, a ground prepolymer or a pearl polymer.

9. The dental material according to claim 1, which comprises
(a) 0.005 to 3 wt.-% of the at least one hydroperoxide,
(b) 0.005 to 3.0 wt.-% of the at least three thiourea derivatives,
(c) 0.00005 to 0.5 wt.-% of at least one transition metal compound,
(d) 5 to 95 wt.-% of at least one radically polymerizable monomer,
(e) 0 to 85 wt.-% of one or more fillers, and
(f) optionally 0.01 to 5 wt.-% of one or more additives, in each case relative to the total mass of the composition.

10. The dental material according to claim 1, which comprises
(a) 0.025 to 2.5 wt.-% of the at least one hydroperoxide,
(b) 0.015 to 2.125 wt.-% the at least three thiourea derivatives,
(c) 0.00025 to 0.25 wt.-% of at least one transition metal compound,
(d) 10 to 95 wt.-% of at least one radically polymerizable monomer,
(e) 0 to 85 wt.-% of one or more fillers, and
(f) optionally 0.1 to 3 wt.-% of one or more additives, in each case relative to the total mass of the composition.

11. The dental material according to claim 1, which comprises
(a) 0.05 to 2.0 wt.-% of the at least one hydroperoxide,
(b) 0.025 to 1.5 wt.-% the at least three thiourea derivatives,
(c) 0.00035 to 0.01 wt.-% of at least one transition metal compound,
(d) 10 to 90 wt.-% of at least one radically polymerizable monomer,
(e) 0 to 85 wt.-% of one or more fillers, and
(f) 0.1 to 2 wt.-% of one or more additives, in each case relative to the total mass of the composition.

12. The dental material according to claim 9, wherein the at least one hydroperoxide comprises cumene hydroperoxide and/or 4-(2-hydroperoxypropan-2-yl)phenyl propionate.

13. The dental material according to claim 1 for therapeutic application as dental cement, filling composite, veneering material or as material for the production of temporary crowns or bridges.

14. A process of using the radically polymerizable dental material according to claim 1, said process comprising
repairing or producing dental restorations comprising prostheses, artificial teeth, inlays, onlays, crowns, bridges or full dentures.

* * * * *